(12) United States Patent
Stanley (10) Patent No.: US 8,398,404 B2
(45) Date of Patent: Mar. 19, 2013

(54) SYSTEM AND METHOD FOR ELEVATED SPEED FIREARMS TRAINING

(75) Inventor: Brian Stanley, Crown Point, IN (US)

(73) Assignee: Conflict Kinetics LLC, Reston, VA (US)

( * ) Notice: Subject to any disclaimer, the term of this patent is extended or adjusted under 35 U.S.C. 154(b) by 696 days.

(21) Appl. No.: 12/202,218

(22) Filed: Aug. 29, 2008

(65) Prior Publication Data

US 2009/0111073 A1    Apr. 30, 2009

Related U.S. Application Data

(60) Provisional application No. 60/969,143, filed on Aug. 30, 2007.

(51) Int. Cl.
*F41G 3/26* (2006.01)
(52) U.S. Cl. .................. 434/22; 434/21; 434/16
(58) Field of Classification Search .......... 434/16, 434/11
See application file for complete search history.

(56) References Cited

U.S. PATENT DOCUMENTS

| | | | | |
|---|---|---|---|---|
| 5,281,142 A | * | 1/1994 | Zaenglein, Jr. | 434/19 |
| 5,417,573 A | * | 5/1995 | Cassiere et al. | 434/21 |
| 6,447,408 B1 | * | 9/2002 | Bonaventura | 473/422 |
| 6,960,085 B2 | * | 11/2005 | Hull et al. | 434/21 |
| 7,396,128 B2 | * | 7/2008 | Feher et al. | 351/205 |
| 7,664,717 B2 | * | 2/2010 | Jenkins et al. | 706/45 |
| 7,841,950 B2 | * | 11/2010 | Davidson et al. | 473/51 |
| 2007/0121066 A1 | * | 5/2007 | Nashner | 351/210 |

OTHER PUBLICATIONS

Laurent Madelain and Richard J. Krauzlis, 2003, Effects of Learning on Smooth Pursuit During Transient Disappearance of a Visual Target, Journal of Neurophysiology, 90:972-982.*
Ritter, F. E., & Schooler, L. J. (2002). The learning curve. In International encyclopedia of the social and behavioral sciences. 8602-8605. Amsterdam: Pergamon.*

* cited by examiner

*Primary Examiner* — Julie Brocketti
(74) *Attorney, Agent, or Firm* — Stewart & Irwin, P.C.; Dennis S. Schell (57) ABSTRACT

The system and method to advance human performance in sighting, tracking, recognizing, and reacting to (collectively "engaging") moving and stationary objects, for example, advancing skill in engaging targets with a firearm. System components include software and hardware that provide target and non-target image stimuli that can be manually or automatically generated as stationary or moving stimuli in a blank or a rendered scene environment. The methods including increase stimuli movement speeds and/or reducing the interval between or the time for which stimuli are displayed until the trainee fails to properly engage the stimuli, then reduce the movement speeds and/or increase the interval time to levels at which the trainee properly engages the stimuli. By repeating training methods with increasing speed, the trainee will be conditioned to achieve proper stimuli engagement with increasingly elevated speed and accuracy.

18 Claims, 10 Drawing Sheets

SYSTEM AND METHOD FOR ELEVATED SPEED FIREARMS TRAINING

CROSS-REFERENCE TO RELATED APPLICATIONS

This application claims the benefit of U.S. Provisional Patent Application No. 60/969,143, filed Aug. 30, 2007, and titled AUGMENTED VISUAL ABILITIES, which is incorporated herein by reference.

BACKGROUND

The present invention relates to human performance training, and particularly, to systems and methods for skills training involving rapid visual and cognitive reactions, for example, rapid sighting, smooth pursuit tracking, object recognition, and reaction skills required for firearms employment.

Firearms are employed for various uses, including for hunting, marksmanship sports, self-defense, police enforcement, and military operations. Traditional firearms training is inherently limited in its ability to deliver quick, high-level advancements in employment skills. Use of live ammunition during training naturally restricts the location, conditions, amount, and types of training that can be safely and economically conducted. Prior art systems and methods for traditional firearms training include live fire training conducted on a traditional shooting range, typically isolated by earthwork berms and using fixed or moving physical targets.

Inherent limitations in traditional firearms training include danger of live fire training; cost of ammunition; lead pollution and cost of lead abatement; firearms preparation and clean up time; time availability of ranges, especially in rifle training; limited multiple target rotation drills; and primitive and cumbersome data collection, analysis, and history of skill such as reaction time and accuracy; minimal elevated targeting (due to bullet trajectory).

More recent firearms training systems and methods include target and combat environments using simulation/gaming platforms, for example, including visual displays for targets and firearms having a laser transmitter in place of projectiles; however, such systems typically lack a methodology and systematic approach needed to achieve heightened performance levels associated with sighting, tracking, recognizing, and reacting to targets over those performance levels achieved with traditional training methods and systems.

SUMMARY

The present invention may comprise one or more of the features recited in the attached claims, and/or one or more of the following features and combinations thereof.

The system and method to advance human performance in sighting, tracking, recognizing, and reacting to (collectively "engaging") moving and stationary objects, for example, advancing skill in engaging targets with a firearm. System components include software and hardware that provide target and non-target image stimuli that can be manually or automatically generated as stationary or moving stimuli in a blank or a rendered scene environment. The methods including increase stimuli movement speeds and/or reducing the interval between or the time for which stimuli are displayed until the trainee fails to properly engage the stimuli, then reduce the movement speeds and/or increase the interval time to levels at which the trainee properly engages the stimuli. By repeating training methods with increasing speed, the trainee will be conditioned to achieve proper stimuli engagement with increasingly elevated speed and accuracy.

System components measure performance parameters such as visual tracking accuracy, sight time, threat recognition and shot accuracy. Hardware includes one or more image projectors, screens, computers, software, laser equipped firearms, laser tracking cameras, eye trackers, and treadmills. Software includes environmental images, stimuli including targets and non-targets, image and target display control, eye movement capture, laser fire capture, and other data capture, analysis, and reporting.

The illustrative embodiment of the present systems and methods is an Elevated Ocular Tactical Conditioning ("EOTC") system, capable of training one or multiple individuals ("trainee") simultaneously. All firearms simulated in the system may be those used for actual employment with the bolt and magazine temporarily replaced with simulation components for use with the EOTC system.

Human perception tends to limit a person to see, react, and engage targets at certain understandable or comfortable speeds. EOTC trainees are conditioned to react upwards of 2 to 3 times faster with heightened awareness and accuracy than achieved with traditional firearms training. The EOTC methods and systems break a trainee's perception of what it believed to be fast, accurate and possible. Once a trainee reaches "mental acceptance" of heightened speed and accuracy, EOTC methods and systems provide the combined mental and physical conditioning needed to consistent achieve heightened performance.

The illustrative EOTC method and system may include hardware and software associated with three types of training:
Kinetic Saccadic Eye Tracker ("K-SET"), used primarily to elevate sighting and tracking performance;
Rapid subject matter recognition ("RSMR"), used primarily to elevate fine motor skills, target and non-target stimuli recognition performance; and
Tactical Ocular Reaction Area ("TORA"), used to elevate all aspects of sighting, fine and gross motor skills and engagement.

Every shot fired is measured, timed, and stored in a trainee's data file. Trainees can review their strengths, deficiencies and performances for various scenarios and for changes in tactics, firearms type, holster type, goggle type, glove type, and the like.

Ocular muscles or saccadic eye muscles can be conditioned to perform like any other muscle in the body. Persons that are trained to see first can then be trained to react first. Training research demonstrates that a person's economy of motion has an enormous effect on their reaction abilities, as well as their radial efficiency to multiple targets. Economy of motion can reduce target acquisition times upwards of one second, which could be the difference between life and death. The present methods and systems provide measurement of baseline performance and training to enhance engagement of stimuli.

A natural deficiency between the eyes and brain is called "visual suppression". Visual suppression exists to stop the visual system from being confused by blurred images that the eye receives while it is moving rapidly from one object or stimulus to another. This suppression presents as a "blackout" of all images between the two stimuli. Most people are unaware of this blackout even though a 90 degree move can be as much as ⅓ of a second with no image. Awareness and training relating to visual suppression heightens firearms performance.

Specifically, it has been discovered that training to sight, track, recognize, and react to stimuli at elevating speeds enables the eyes to develop strength and agility like any other part of the body, naturally heightening visual speeds and abilities while reducing the visual suppression area. Upwards of 200% increase in performance after six 30 minute training sessions have been achieved. Methods include having the eyes start tracking at a slow reasonable speed, gradually elevating to impossible speeds, and finally slowing down to a slightly more comfortable speed. Including the three illustrative K-SET, RSMR, and TORA scenarios, the EOTC includes visually acquiring 1010 targets and firing 530 virtual rounds around a 220° area, capturing and analyzing data, while taking only 30 minutes to complete.

Additional features of the disclosure will become apparent to those skilled in the art upon consideration of the following detailed description of the illustrative embodiment.

BRIEF DESCRIPTION OF THE DRAWINGS

The detailed description particularly refers to the accompanying figures in which.

DESCRIPTION OF THE ILLUSTRATIVE EMBODIMENTS

For the purposes of promoting and understanding the principals of the invention, reference will now be made to one or more illustrative embodiments illustrated in the drawings and specific language will be used to describe the same.

The disclosed methods and systems for displaying a series of static and/or moving visual stimuli to a trainee are used to conditioning an enhanced trainee engagement of the stimuli. The engagement skills being conditioned for a particular embodiment of the disclosed methods and systems may be one or more than one of sighting, tracking, recognizing, and reacting to visual stimuli. For example, the engagement conditioned in first embodiment can be limited to simply the training sighting and tracking a sequence of moving targets on a visual display(s) and measuring the trainee's performance. For example, the engagement skills conditioned in a second embodiment can be sighting, tracking, and recognizing threat and non-threat targets on a visual display(s) and measuring the trainee's. And for example, the engagement skills conditioned in a third embodiment can be sighting, tracking, recognizing, and reacting to, for example firing on threat and not firing on non-threat targets and measuring the trainee's performance.

Figure 1:
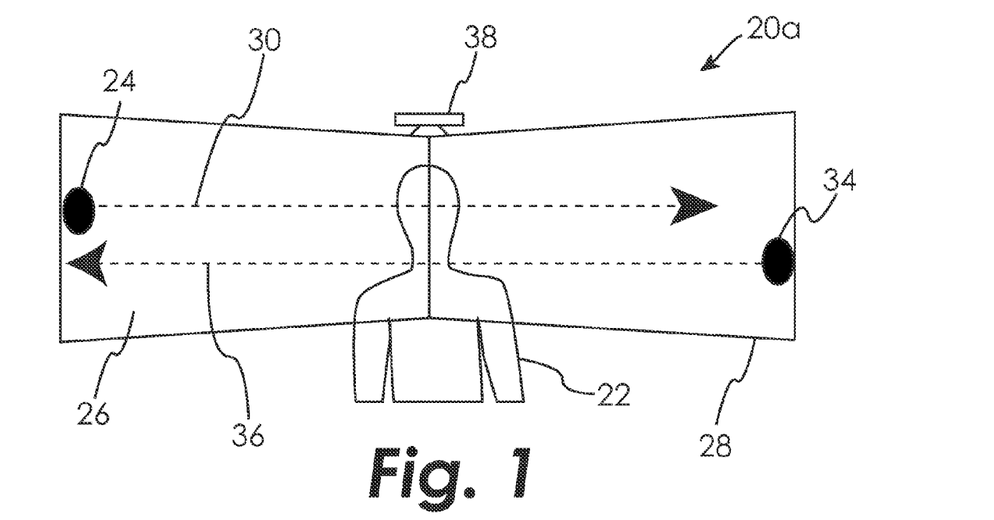
FIG. 1 shows a display portion and illustrative stimuli of an illustrative embodiment of a method and system for EOTC according to the present disclosure, for example for K-SET training.

For example, as shown in FIG. 1, for a first illustrative system and method 20a for EOTC, a trainee 22 is conditioned by displaying a first target (stimulus) 24 adjacent the left side of one or more displays 26 and 28 and the first target 24 subsequently moving rapidly in a straight line pattern 30 to the right side of the displays 26 and 28. After a delay interval, for example 0.50 seconds, a second target (stimulus) 34 can be displayed adjacent the right side of displays 26 and 28, pause for a present or random amount of time, then move rapidly in a straight line pattern 36 to the left, at a speed greater than that of pattern 30 for target 24. Subsequent targets (not shown) can follow an identical or alternative pattern of movement and delay and incrementally increasing speeds making it difficult for the trainee 22 to accurately sight and track the subsequent targets. An ocular tracker 38 can be used to determine the trainee's performance in sighting and tracking targets.

Figure 2:
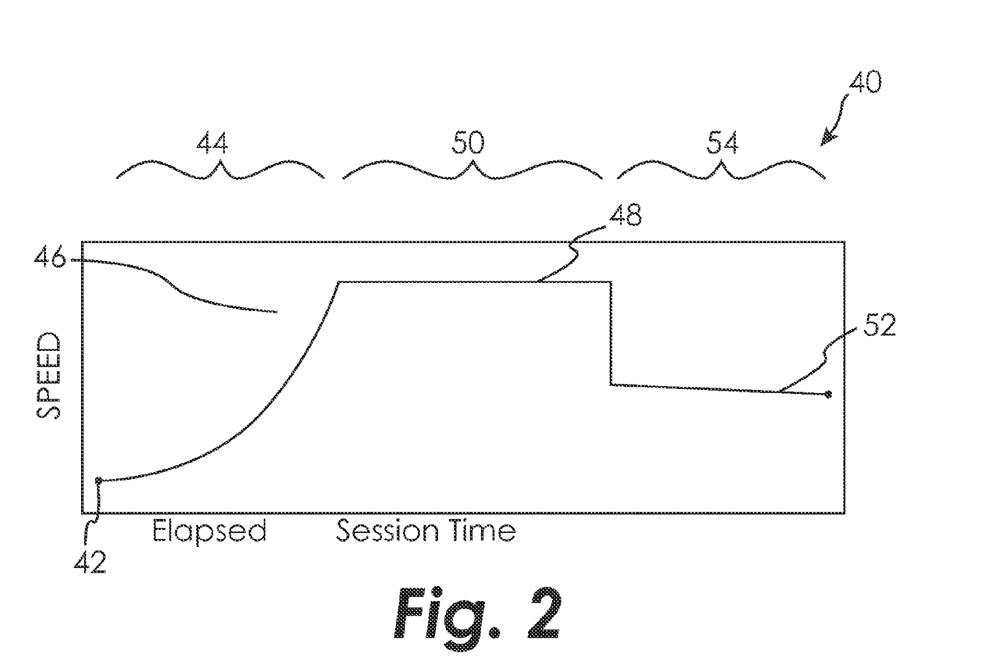
FIG. 2 is a graph illustrating phases of training associated with the illustrative embodiments of the method and system for EOTC.

Referring to FIG. 2, the graph of target speed vs. elapsed time associated with the illustrative system and method 20a, shows various phases of a training session 40. After an initial speed 42 associated with the first target 24, a period 44 of incrementally increasing speed is used for the second target 34 and subsequent targets (not shown), making it more more difficult for the trainee 22 to sight and track the targets. After a threshold speed or percentage 46 at which the trainee 22 can no longer consistently and accurately track targets, a set speed 48 is used for subsequent targets during a plateau period 50. For example, a threshold percentage may be, for example, 50%, 25%, or 10%. After the plateau period 48, for example a specific period of time, for example 45 seconds, or a specific number of targets, a comfortable speed 52 is used for subsequent targets during a final period 54.

Additionally or alternatively, the interval between appearance and movement of subsequent targets can be gradually decreased during the increasing period 44, thus making the threshold 46 at which the trainee can no longer accurately sight and track targets a combination of target speed and delay interval.

Figure 3:
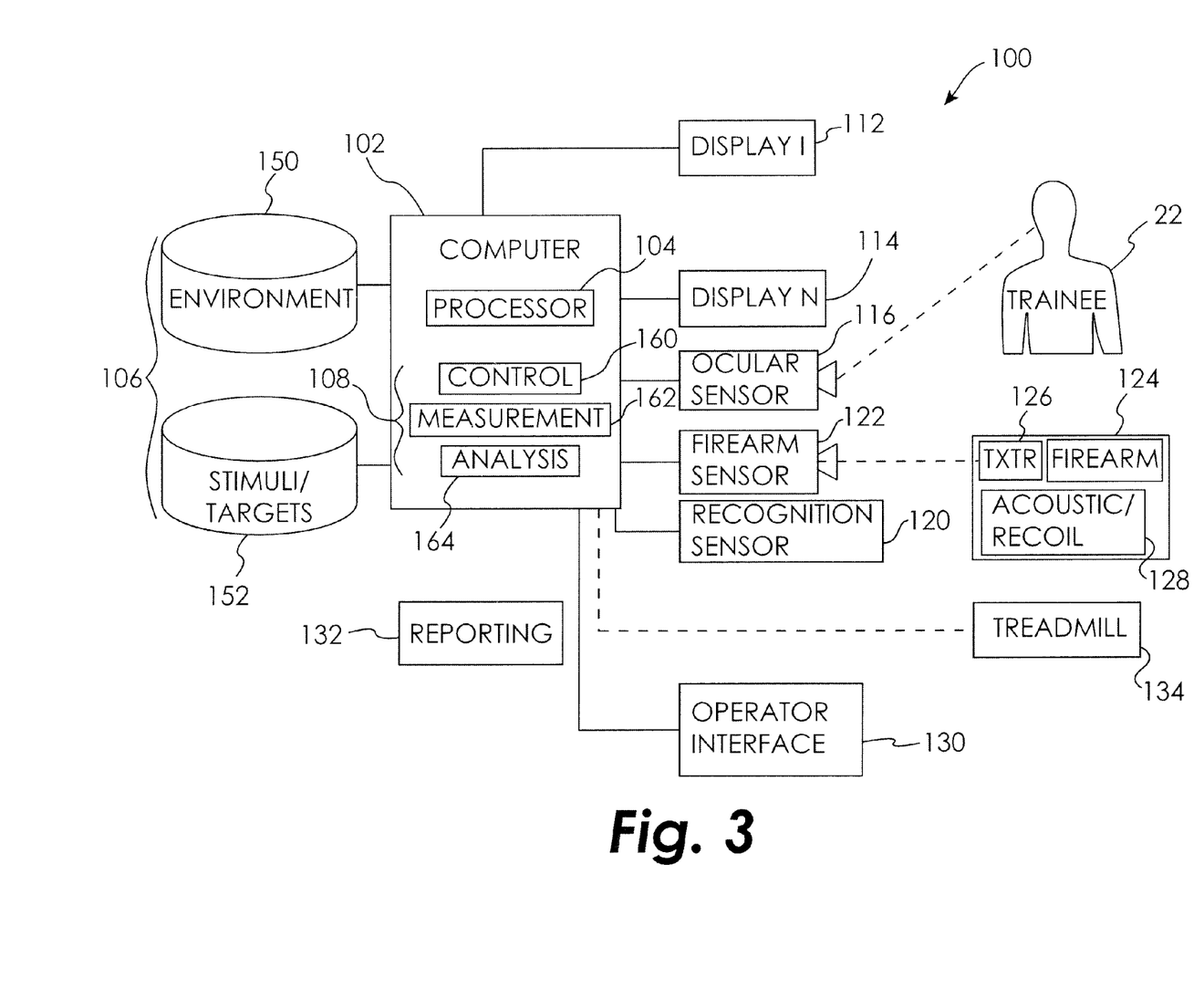
FIG. 3 shows another illustrative system for EOTC according to the present disclosure.

FIG. 3 shows another embodiment of a system 100 for EOTC of trainee 22. The system 100 generally includes a computer or network of computers 102 having one or more processors 104, data 106, and software 108, one to N displays 112 and 114, and an ocular sensor 116 for determine eye gaze and tracking of trainee 22, for example, systems such as those available from SensoMotoric Instruments of Boston, Mass., and SR Research of Osgoode, Ontario, Canada.

The system 100 may also optionally include a recognition sensor 120, for example, capable of registering a trainee's recognition of a target as a threat or non-threat. For example, the recognition sensor 120 may include a simple input switch (es) such as computer mouse buttons used by trainee 22 to register recognition, or an input sensor requiring processing, for example a voice recognition capable of deterring recognition based on a trainee's audible/verbal response.

The system 100 may also optionally include a firearm sensor 122 for detecting the firing and aim of a firearm 120 used by the trainee 22. Firearm 120 can be a simulated firearm, or an actual firearm modified for training use, for example, by replacing the bolt and magazine with a transmitter 126, for example a laser emitter, and a gas discharge device 128 for providing action of the firearm mechanism and simulated acoustics and recoil of firing.

The system 100 may also optionally include an operator interface 130, for example coupled with the computer 102 and providing control of various components of system 100 and/or monitoring of the trainee's performance. The system 100 may also optionally include performance reporting 132, for example visual and/or data output from the computer 102. The system 100 may also optionally include a treadmill 134 to simulate foot travel for trainee 22. Additionally, the system 100 may also include addition sensors 116, 120, 122, operator interfaces 130, firearms 124, and treadmills 134, for example, to support training of multiple trainees 22 simultaneously.

Figure 5:
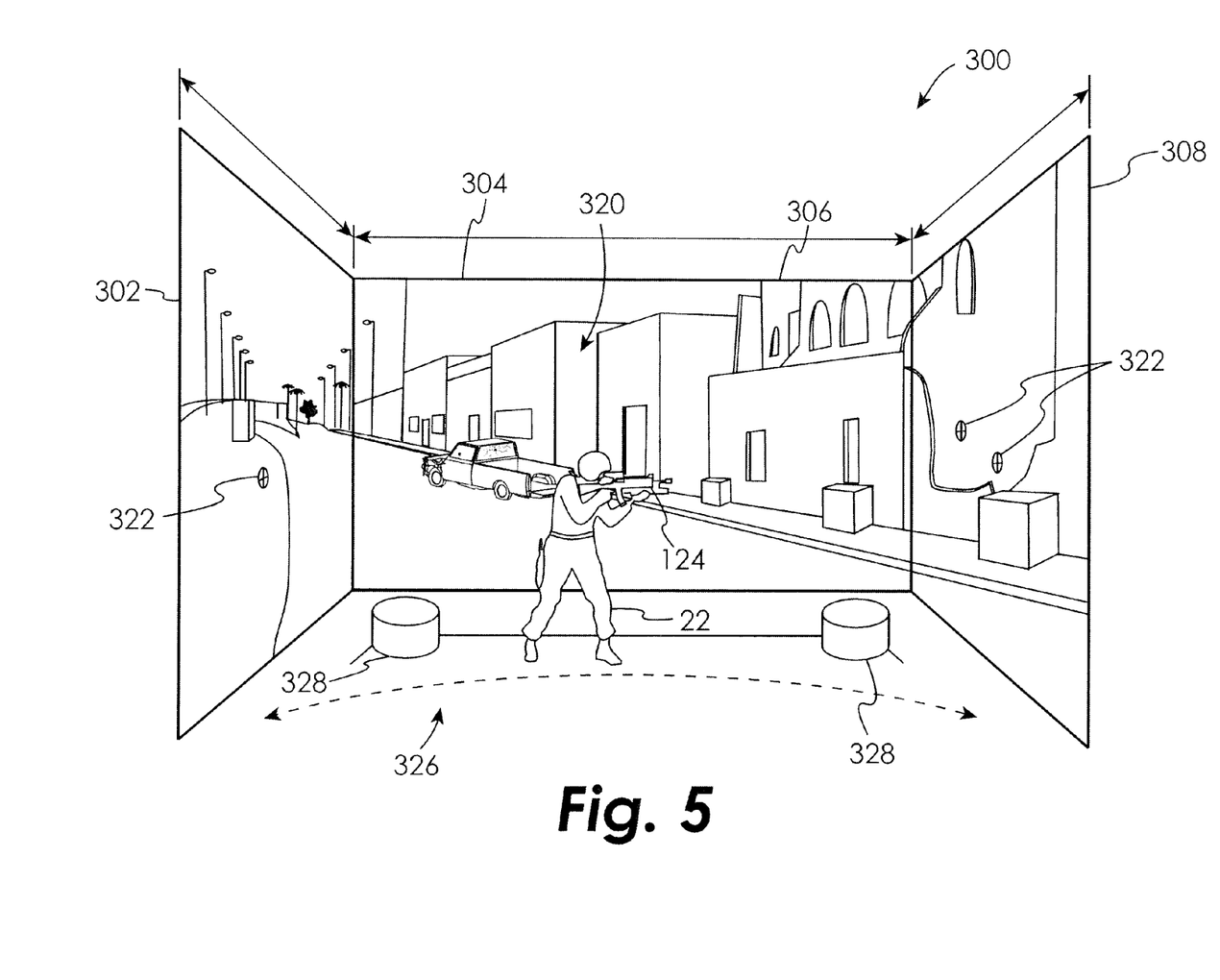
FIG. 5 shows a display portion of another illustrative system for EOTC, for example for TORA training.

Some embodiments of the system 100 include only those components required for the particular and more limited EOTC training scenario, for example, as shown in FIGS. 1 and 2 for Kinetic Saccadic Eye Tracker ("K-SET") training, used primarily to elevate sighting and tracking performance, or for Rapid subject matter recognition ("RSMR") training shown in FIG. 3 used for used primarily to elevate target and non-target stimuli recognition performance. Such embodiments of the system 100 can lack various optional components, for example, the firearms sensor 122, firearms 124, and treadmill 134, and various components of the data 106 and software 108. Other embodiments of system 100 are more robust, would typically include all the components shown in FIG. 3 and support a full range of EOTC training scenarios, for example, such an illustrative system 200, a portion of which is shown in FIG. 5, used for Tactical Ocular Reaction Area ("TORA") training to condition and elevate all aspects of firearms employment and engagement.

Figure 4:
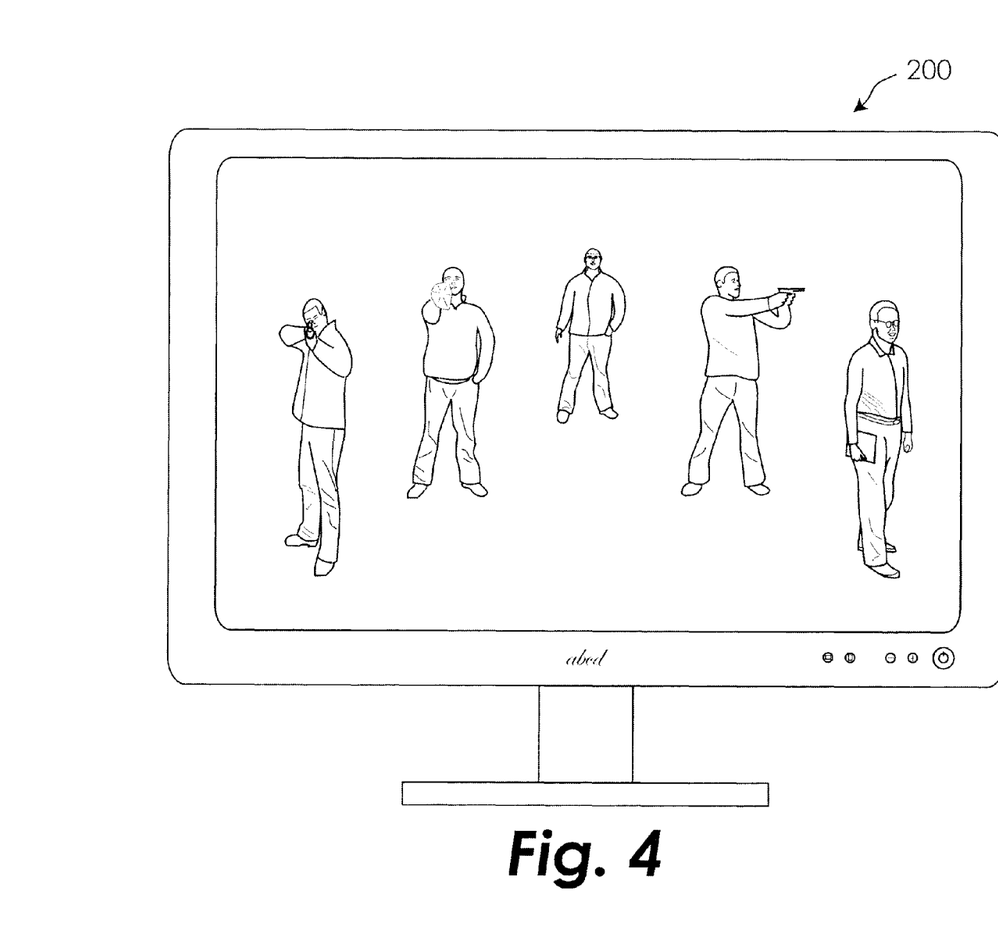
FIG. 4 shows a display portion of another illustrative system for EOTC showing different illustrative images used for RSMR training.
Figure 6:
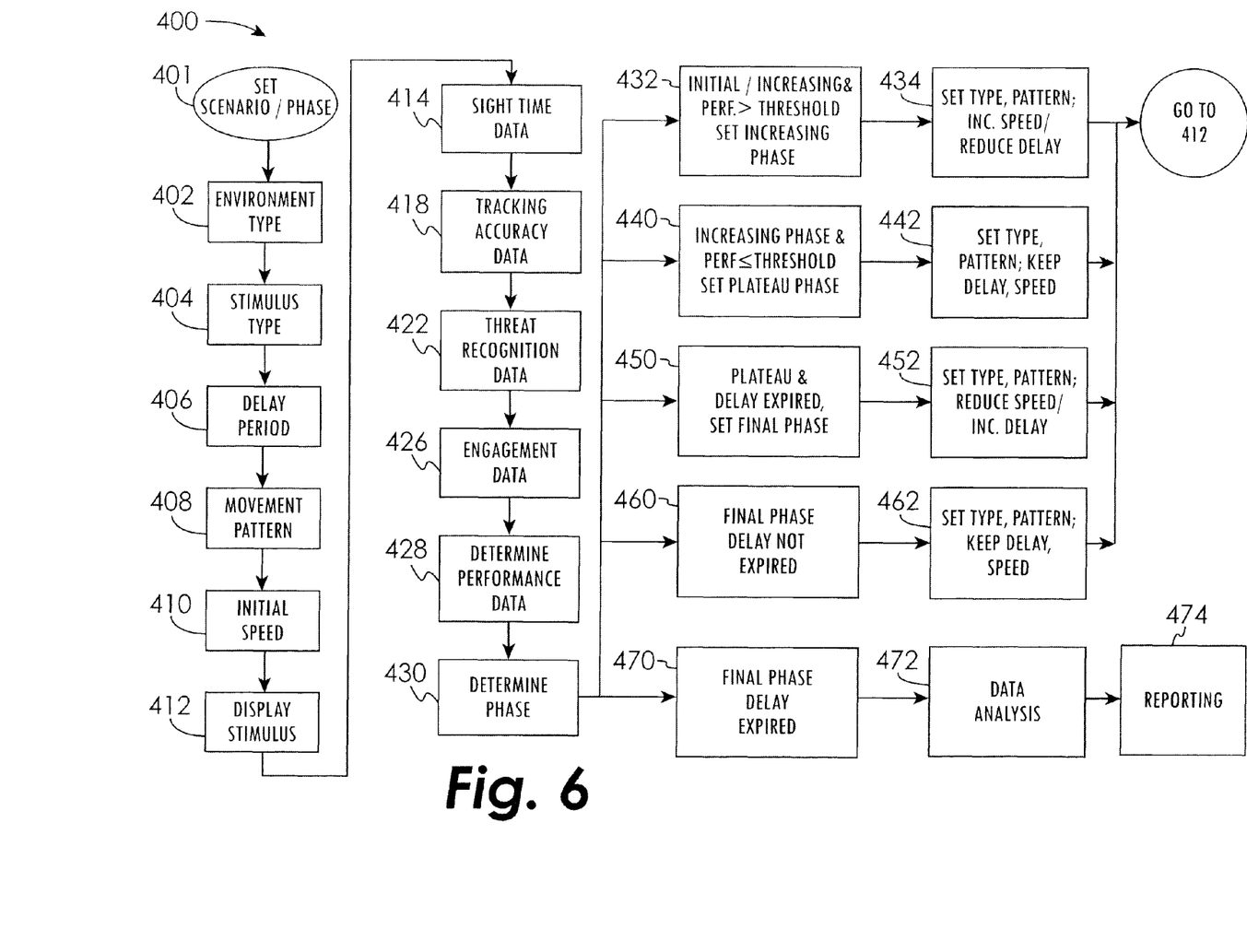
FIG. 6 shows an illustrative process associated with the methods and systems for EOTC according to the present disclosure.

FIG. 6 shows a first illustrative method 400 that can be used with the illustrative systems 20a/b, 100, 200 and 300 for displaying a series of static and/or moving visual stimuli, for example targets, to a trainee for conditioning an enhanced engagement of the stimuli. In step 401, a Training Scenario is selected and the training Phase set, for example to Initial for some scenarios, or to Final for scenarios using a fixed speed and delay for subsequent targets. In step 402, a display scene or Environment Type is selected and displayed, for example, an empty (blank) scene as shown in FIG. 4, or an urban scene as shown in FIG. 5. In step 404, a Stimulus Type to by displayed is selected, for example a human form with or without a threat, for example a firearm. In step 406, an initial Delay Period from 0 seconds to a present or random length of time is determined. For example, the Delay Period can be used to determine the length of time before a stimulus is displayed, the length of time the stimulus is displayed, or the length of time a particular set of stimulus at a particular speed are displayed. In step 408, an initial Movement Pattern of the stimulus is determined. The Movement Pattern may specify not only the pattern in which a stimulus moves (or does not move), but also the relative displacement or location on the displays 26 and 28 of a stimulus relative to the prior stimulus, for example, as shown in FIGS. 10-15 and further described below. In step 410, an initial Speed of the stimulus is determined, for example, the Speed can be the speed at which a stimulus moves on the displays 26 and 28.

In step 412, the stimulus is displayed to a trainee according to the Stimulus Type, Delay Period, Movement Pattern, and Speed. For example, during the initial Delay Period the stimulus may be not displayed, or the stimulus may be displayed but remain static relative to the trainee. For the initial Movement Pattern, for example, the stimulus may move in a straight line relative to the trainee, for example, moving along a horizontal axis at substantially fixed distance relative to the trainee, or may be a fixed, non-moving stimulus. The initial Speed and/or Delay Period are generally selected as a relatively easy speed for the trainee to sight and visually track the stimulus, for example, movement at 10 degrees/second or subsequent stimulus at 1.5 seconds intervals.

In step 414, it is determined how long the trainee took to sight the stimulus. In step 416, Sight Time data is stored relating to the time it took the trainee to sight the stimulus. In step 418, it is determined whether the trainee remains focused on (tracks) the stimulus. In step 420, Accuracy data is stored relating to the trainee's accuracy in tracking the stimulus. Optionally, in step 422, it is determined whether the trainee properly recognizes the stimulus, for example as a threat or non-threat. In step 424, Recognition data is stored relating to the trainee's recognition of the stimulus. Optionally, in step 426, it is determined whether the trainee properly engages the stimulus, for example, accurately fires at the stimulus. In step 424, Engagement data is stored relating to the trainee's engagement. Optionally, in step 428, Performance data is determined as a function of Sight Time, Accuracy, Recognition, and/or Engagement data.

In step 430, the Phase of the training scenario is determined, for example, Initial, Increasing, Plateau, Final, or Complete.

If the present Phase is determined to be Initial or Increasing and Performance is greater than a preset Threshold, then in step 432, the Increasing phase is set. In step 434, a subsequent Delay Period, Stimulus Type, Movement Pattern, and Speed is determined for the Increasing Phase. For example, as shown in FIG. 2, the Speed of the stimulus movement may be steadily increased for each subsequent display, for example, movement in increments of 10 degrees/second. Additionally or alternatively, the Delay Period may be steadily decreased for each subsequent display, providing a short and short time interval during which a stimulus is displayed, for example, in increments of 0.25 seconds. After step 434 is completed, the method returns to step 412 to display the subsequent stimulus.

If in step 430 the present Phase is determined to be Increasing and the Performance is equal to or less than Threshold, then in step 440 the Plateau phase is set.

If the present Phase is Plateau and a present Plateau Delay has not yet expired, for example, 45 seconds or a present number of subsequent stimuli, then in step 442 the subsequent Stimulus Type and Movement Pattern are determined and the Delay Interval and Speed remain the same. After step 442 is completed, the method returns to step 412 to display the subsequent stimulus.

If the present Phase is Plateau and a present Plateau delay has expired, then in step 450 the Phase is set to Final. In step 452, the subsequent Stimulus Type and Movement Pattern are determined and the Delay Interval and Speed are set to a selected level that provides a higher Performance than the trainee achieved in the Plateau Phase. For example, stimulus speed/frequency in the Final Phase may be selected by the operator based on the trainee's performance, or may be calculated as a function of performance and/or other data collected during the session. After step 452 is completed, the method returns to step 412 to display the subsequent stimulus.

If the present Phase is Final and a present Final Delay has not yet expired, for example, 30 seconds or a present number of subsequent stimuli, then in step 460 the subsequent Stimulus Type and Movement Pattern are determined and the Delay Interval and Speed remain the same. After step 460 is completed, the method returns to step 412 to display the subsequent stimulus.

If the present Phase is Final and a present Final Delay has expired, then in step 470 training is complete and final data analysis and reporting is completed.

For example, as shown in FIGS. 2 and 3, a single Stimulus Type and Movement Pattern may repeated but an incrementally increasing Speed and/or reduced Delay Period applied until the trainee's Performance drops below a selected Threshold. After reaching the Threshold, the Speed/Delay Period combination can be maintained for a present Plateau Delay, then the Speed is reduced and/or the Delay Period lengthened to provide a higher Performance and that Speed/Delay Period maintained for a present Final Delay.

The Environment and the initial and sequence of subsequent Stimulus Types, Delay Periods, Movement Patterns, and Speeds may be predetermined by the Training Scenario selected in Step 400. Alternatively or additionally, one or more of these variables may be determined by the trainee's Performance. Alternatively or additionally, one or more of these variables may be determined by an Operator, including in response to the trainee's Performance during the scenario.

K-SET: Kinetic Saccadic Eye Tracker

An embodiment of the illustrative system 100 and the illustrative method 400 can be used to implementing K-SET training, which is used primarily to elevate sighting and tracking performance of the trainee 22.

For example, referring to FIG. 2, a 2-minute K-SET session can be performed by using an increasing period 44 lasting about 45 seconds, a plateau period 48 lasting about 45 seconds, and a filial period 54 lasting about 30 seconds. The displays 112 and 114 used for the K-SET session can be, for example, high refresh rate 52 inch plasma flat-panel monitors. Computer 102 can be a standard PC type computer having an operator interface 130 consisting of, for example, a keyboard, pointing device, and monitor.

The displays 112 and 114 are arranged as shown for displays 26 and 28 in FIG. 1, abutted end to end, the faces of the displays forming an obtuse angle, the interior of which faces the trainee 22. The angle of the display faces and the trainee 22 position relative to the displays 26 and 28 (112 and 114) can be such that the trainee 22 can track targets 24 and 34 through 180 degrees or more motion. For example, the trainee may be positioned approximately 18 inches from the displays 26 and 28.

Saccades are used to bring the eye rapidly from one point of regard to another. Because the eyes do not see during a saccade, it is best to get them over as quickly as possible. Accordingly, saccades typically move at speeds between 200 and 600 degrees/sec—for 300 deg/sec, to move gaze 90 degrees, it takes about ⅓ seconds, which is a long time not to see when in a threat environment.

K-SET enhances performance in various ways. For example, trainee 22 is conditioned to keep the eyes open and focused throughout the motion patterns 30 and 30 of the targets 24 and 34. Benefits of this conditioning include, for example, increasing visual awareness of soldiers and law enforcement officers in clearing rooms, engaging multiple targets in close quarters, and in high speed pursuits and the like. The conditioning also strengthens the muscles in the eyes so that the speed at which the trainee 22 can focus on multiple objects in an urban warfare situation is increased.

Optionally, the trainee 22 can walk on a treadmill 134 (FIG. 3) in front of the displays 112 and 114 in order to condition sighting and tracking during "smooth pursuit". Additionally or alternatively, the speeds of subsequent targets during a K-SET session can be set to increasing and decreasing speeds. For example, ten target velocities (ranging from 10 to 100 deg/s in 10 deg/s increments) presented in random order with each target velocity being repeated 20 times.

An operator using operator interface 130 can manually begin and can manually control the type of targets and the speed and interval between targets. For example, the type of target displayed can be fixed as a ball or be selected from other objects or shapes and subsequently varied.

The software 108 uses a comparison of the location of the target 24 or 34 on the displays 26 and 28 and data collected from the ocular sensor 116, which indicates the gaze and track of the trainee's eyes, to determine whether the trainee 22 is focused on and tracking the target 24 or 34 or is not able to track the target 24 or 34. The software 108 determines and collects data relating to the trainee's accuracy in tracking the target 24 and 34.

The adjustments in the subsequent target speed and/or the delay interval between targets can be automatically set by the software 108 or manually by the operating. For example, adjustments can be determined based on a preset profile associated with the training scenario selected the trainee's accuracy, the trainee's accuracy, or other factors considered by the software 108 or operator; however, all profiles provide subsequent targets at a speed and/or delay interval 48 (FIG. 2) during the plateau period 50 that exceed the trainee's ability to consistently and accurately sight and track, and subsequent targets at a speed and/or delay interval 52 for a final period 54 that the trainee can consistently and accurately sight and track with reasonable comfort.

Figure 7:
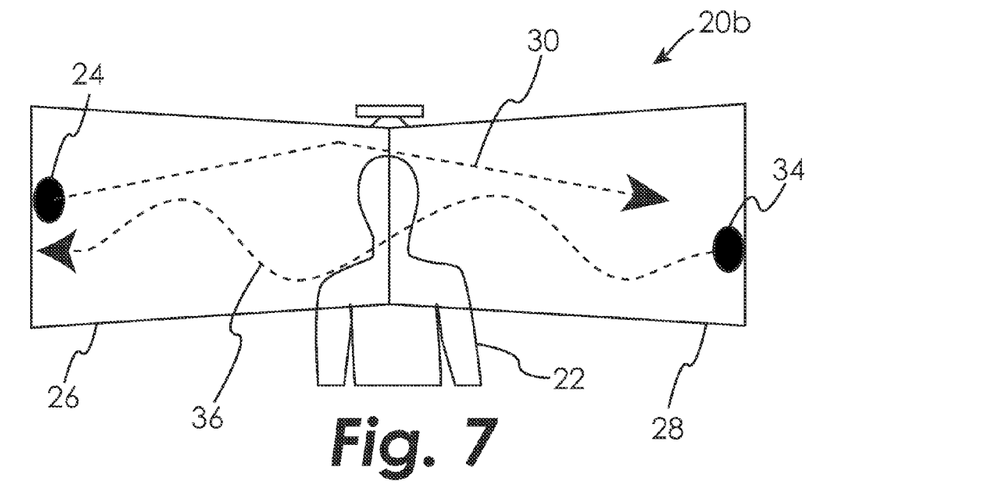
FIG. 7 shows a display portion and illustrative stimuli of another illustrative embodiment of a method and system for EOTC according to the present disclosure, for example for K-SET training.

Additionally or alternatively, as shown in FIG. 7, in an illustrative system and method 20b, the movement patterns 30 and 36 (and patterns of subsequent targets) can include patterns other than a straight line, for example, angled, arcing, and/or complex patterns. The presentation of patterns can be random, pre-defined, based on performance of the trainee, or selected by the operator.

Additionally or alternatively, the patterns associated with the illustrative system and method 20b can in the targets 30 and 36 making random path changes, that include immediate or gradual changes of direction at angles such as 36, 45, 90, 126, and 180 degrees, and/or the targets 30 and 35 stopping movement and subsequently restarting movement.

Additionally or alternatively, the illustrative system and method 20b can include images flashed on the displays 26 and 28 to condition recognition/situation awareness. For example, the method may include the trainee 22 providing a different responses using recognition sensor 120, for example, the switches on a computer mouse. For example, if a displayed image includes a person holding an object of threat, for example a firearm, the trainee 22 is instructed to press the left mouse button immediately upon recognition, or the right mouse button if there is no threat. The trainee may also be asked questions regarding physical features of the image/person to help condition situational awareness.

RSMR: Rapid Subject Matter Recognition

An embodiment of the illustrative system 100 and the illustrative method 400 can be used to implementing RSMR, which is used primarily to elevate target and non-target stimuli recognition performance. Referring to FIG. 2, for example, RSMR conditioning can be performed by using an increasing period 44 lasting about 45 seconds, a plateau period 48 lasting about 45 seconds, and a final period 54 lasting about 30 seconds. The embodiment of system 100 for completing RSMR conditioning can be, for example, the same embodiment as described for K-SET conditioning above, including the arrangement of plasma displays 26 and 28 shown in FIG. 1.

For example, referring to FIG. 4, the illustrative system 200, can be used for RSMR conditioning in which the software 108 displays human images, for example, a single actor filmed and or photographed in numerous images of varied positions, but wearing the same clothes, with some images presenting various levels of threat, for example holding a firearm, and other images not presenting a threat.

Figure 8:
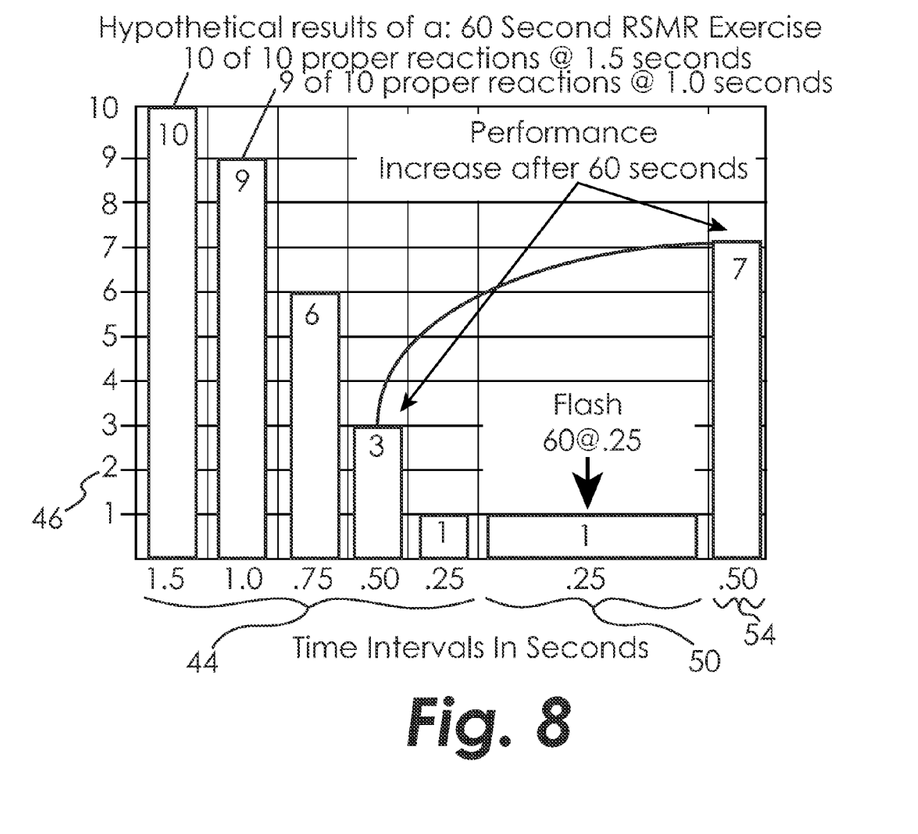
FIG. 8 shows an illustrative training scenario and results associated with the methods and systems of the present disclosure.

Referring to FIGS. 2 and 8, the speed of movement of the stimuli in the RSMR is the time interval for which the images are displayed. For example, the display interval can begin at 1.5 seconds and the interval incrementally decrease (speed at which new images are displayed increases) during the increasing phase 44, for example to a 0.25 seconds interval during the plateau phase 50, and then to 0.50 seconds interval during the final phase 54. As with K-SET, the trainee 22 can provide an input to the recognition sensor 122 (FIG. 3), for example a particular button on a computer mouse button, depending on whether an image presents a threat or not. The elevating speed methodology is used to condition the brain to function at elevated speeds. Additionally, as with K-SET, the target images can be stationary or moving, and subsequent images can be angular displaced from prior images.

As shown in FIG. 8, by using progressively increasing speeds during the increasing phase 44, for example, interval times of 1.5, 1.0, 0.75, 0.50, and 0.25 seconds, after reaching 0.25 seconds, the trainee's performance accuracy below a preset threshold 46, for example, only 10%. An additional 60 images are flashed for 0.25 seconds each during the plateau phase 50. The final phase may be, for example, at 0.50 seconds and trainee 22 is expected to experience an improved accuracy of two or three times that experienced at the same speed during the increasing phase 44. For example, in the hypothetical results shown in FIG. 8, the trainee's accuracy at 0.50 seconds interval increases from 30% to 70%. Additional measurements made by the system 100 may include parameters such as reaction time, saccadic accuracy, saccade-evoked blinks, and eye velocity.

TORA: Tactical Ocular Reaction Area

An embodiment of the illustrative system 100 and the illustrative method 400 can be used to implementing Tactical Ocular Reaction Area ("TORA") condition, which is used to elevate all aspects of engagement, for example, engagement of targets with firearms. TORA can utilize a sequence of conditioning drills scenarios, for example, the 22 illustrative drills discussed below.

The illustrative scenarios were developed to locate and otherwise present the targets in a way that conditions heighten vision, physical reaction, and economy of motion against single and multiple target engagements. In the TORA phase trainees engage hundreds of targets, often from uncomfortable and challenging angles. Trainings escalate in difficulty with no ceilings. As trainees excel in one sequence, speeds will increase and target size will decrease, arm weights, hand weights, wobble boards, treadmills, and stimuli are added to create an even faster more focused trainee 22.

An illustrative embodiment of the system 100 for TORA conditioning is the TORA system 300 shown in FIG. 5. In system 300, the displays 112 and 114 typical of system 100 include one or more projectors (not shown) and projection screens 302-308. For example, PT-5600 UL projectors with ET DLE 50 short throw lenses available from Panasonic, Secaucus, N.J. can be used to project environmental images 320 and targets 322 against a surface, for example, prepared, flat, interlocking screens or walls measuring approximately 10 feet by 10 feet. Typically, a projector would be associated with each of the screens 302-308. However, non-flat surfaces, varied dimensions, rear projection, and other techniques and/or additional and/or alternative display features known in the art may be utilized.

An interior area 326 within which the trainee 22 may move and employ the firearm 124 is generally defined by the perimeter of the screens 302-308. For example, the trainee 22 is circumscribed by screens 302-308 by at least about 220 degrees; however, the system 300 may provide a lower angular view or may circumscribe the trainee by a full 360 degrees. Additionally, display of environmental scenes 320 and targets 322 may extend above normal ceiling heights and below the normal floor plan, for example, extended by an additional 10 foot in the vertical above or below one or more of the screens 302-308 by associating additional screens (not shown) with the system 300. The area 326 may also include environmental objects, for example obstacles 328 and one or more treadmills 134 (FIG. 3).

Firearm 124 can be a standard firearm, for example semi-automatic handgun or rifle, reversibly modified to remove live firing and add a transmitter 126, for example a laser emitter, and optionally a gas system 128 for simulating mechanical action, recoil, and acoustics associated with live fire. For example, transmitters 126 and gas systems 128 available for reversibly modify firearms 124 from Dvorak Instruments of Tulsa, Okla.

The firearm sensor 122 for detecting and locating the laser shot fired by firearms 124 on screens 302-308 may be one or more area scan cameras directed at the screens 302-308, for example, model number A602 available from Basler Vision Technologies of Exton, Pa., used with a visible light filter lens to remove environmental images and isolate the laser light projected by firearm transmitter 126. Processing and analysis of the targets 322 and measurement and performance relating to shots against them using the firearm 124 may be facilitated by the software 108 identifying and utilizing subdivisions within each screen 302-306. For example, software 108 can divide each screen 302-308 into four equal quadrants (not shown) to facility mapping, measuring, and analyzing target sequences and performance. For example, the relative displacement of sequential or simultaneous targets from one to another adjacent or non-adjacent quadrant may be used to determine a measure of difficulty associated with successfully engaging both targets.

Targets displayed with the environmental scene images may be digitally added and projected by the above described projectors (not shown) of displays 112 and 114, or may be separately displayed on screens 302-308, for example, using one or more separate motorized projectors (not shown). Advantageously, comparison of location and expanse of targets 322 on screens 302-308 and the projection location on screens 302-308 of the laser fired by firearm 124 (as captured by sensor 122) is used to determine the time to react and engage and the accuracy of shot, including a hit or miss.

Figure 9:
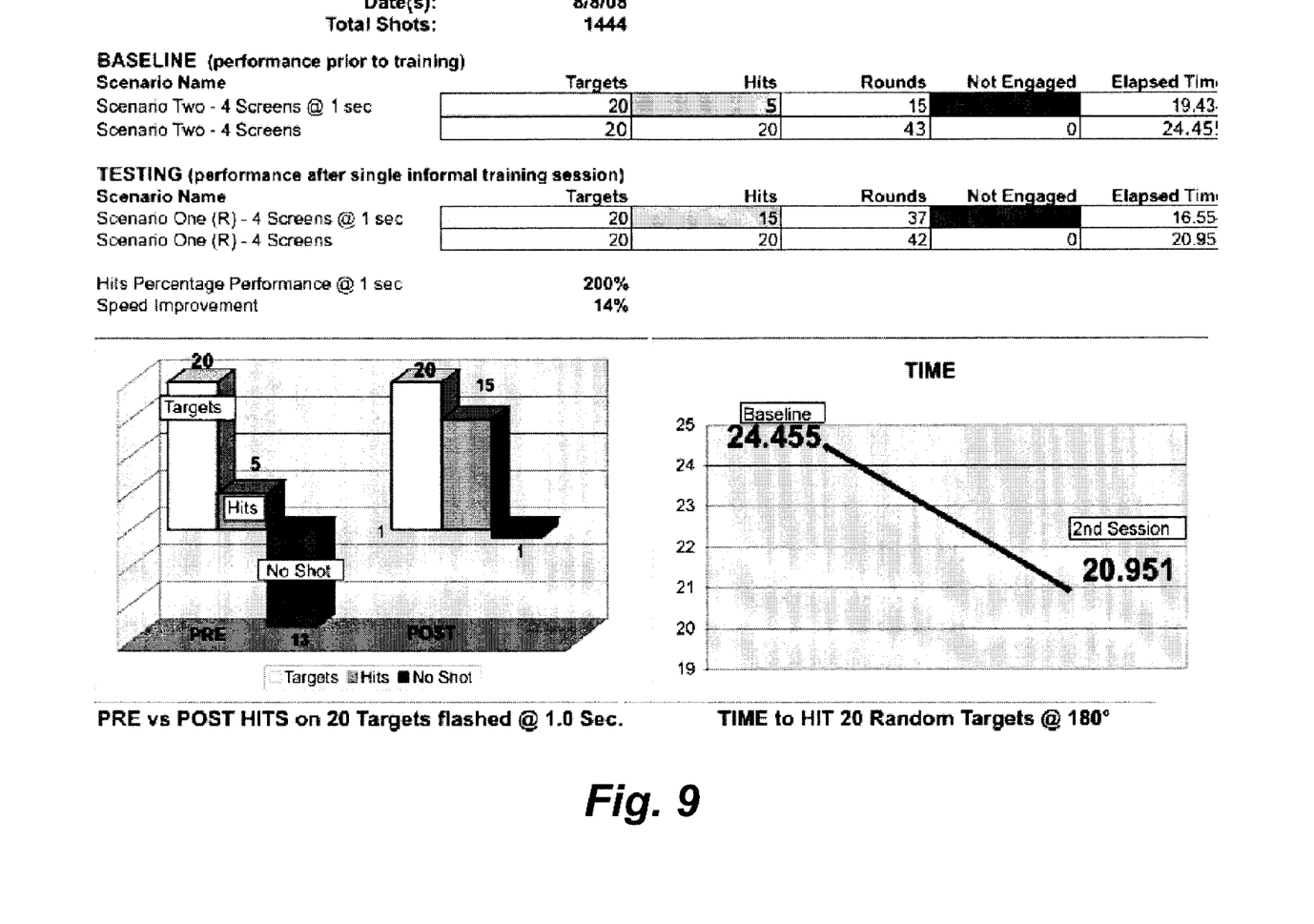
FIG. 9 is an illustrative report produced by the methods and systems of the present disclosure.

In the illustrative embodiment 300 of system 100, computer 102 may include multiple networked computers (not shown) to manage the components and processing of the system. Additionally, or alternatively, a WAN (not shown) such as the internet may be used to provide remote processing power or service of the data 106 and software 108. The data 106 includes an environment database 150 for projecting images 320, for example stills, video, or graphically rendered images of background scenes. The data 106 also includes a stimuli or target database 152 for projecting targets 320, for example stills, video, or graphically rendered images of threat and non-threat people, vehicles, and the like. The software 108 executed by the processor 104 includes control software 160 for displaying scenes 320 and targets 322 and for providing the training scenario, such as method 400 implementing the below described scenario drills. The software 108 also includes measurement software 162 to facility capture and processing of data, for example, from sensors 116, 120, and 122. The software 108 also includes analysis software 164, for example, for analyzing captured scenario and performance data and producing reporting 132, for example, the illustrative TORA Performance Report shown in FIG. 9. Additional reporting may include, for example, a listing of trainee ID, scenario ID, firearm ID, timestamps, targets presented, targets hit, "rounds" expended, targets not engaged, elapsed time, and other scenario and performance data and analysis, including for example aggregate, average, and improvement in performance data. The software 108 may include adapted commercially available software, for example MATLAB for various functions of measure software 162 and Microsoft Excel for various functions of analysis software 164.

TORA Illustrative Training Modes

Two training modes may be used to present targets and determine sequencing of targets 322, fixed and open intervals.

For the fixed intervals target mode, a sequence of targets 322 appear for a fixed time interval in predetermined locations on screens 302-308. The targets 322 remain static and then are removed from view after expiration of the fixed interval of time. For example, each of 20 targets appear one at a time in sequence for 1.0 seconds each. Each target remains visible until successfully engaged (fired upon) or until the expiration of the fixed interval of 1.0 seconds.

For the open interval target mode, targets 322 appear in predetermined locations on screens 302-308 and remain displayed until successfully fired upon. After being successfully hit, the subsequent target 322 appears and remains visible until successfully fired upon.

Illustrative TORA Training Scenarios/Patterns

Various fixed conditioning sequences or scenarios that provide a pattern of targets 322 and require the trainee 22 to perform various skills conditioning tasks are used, including the incorporation of increasing the speed of target displays (shorter intervals) to an impossible level as the scenario or sets of scenarios used proceed, then reducing the speed to an achievable level, for example, as described above for the methods associated with the K-SET and RSMR training. For example, in TORA, the method 400 can include a set of 20 targets 322 are displayed for a display interval of 1.5 seconds around the full angular range of screens 302-308, whether vertically displaced, or along a set height (or horizontal plane). Next, a set of 20 targets appears at 1.0 second intervals, then 0.75 seconds, then 0.50 seconds, then 0.25 seconds. At the 0.25 seconds target interval, the targets 322 appear to most trainees 22 as too rapid to engage, and appear way to fast to shoot at. By exposing the trainee 22 to these elevated speeds, when the speed is slowed, the trainee 22 is able to accurately engage targets 322 at higher speeds than before being conditioned at the elevated speeds. Various other conditioning drills can be used as part of a training session, for example, before and after elevated speed scenario drills.

Scenario 1, Draw, 20-Front: The drawing of firearm 322 from a holster to a ready position, or from a rest to a ready position for non-holstered firearms 322 is conditioned in the draw scenarios. For example, for draw 20-front, the trainee 22 faces forward, for example, toward screens 304 and 306, a target 322 is displayed on screens 304 and 306, the trainee 22 readies firearm 124, for example drawing it from a holster, sights, and fires upon the target 322. The process repeats to engage a total of 20 targets, for example, displayed on screens 304 and 306.

Scenario 2, Draw, 20-Left: The trainee 22 faces forward, for example, toward screens 304 and 306, a target 322 is displayed on left-hand screen 302, the trainee 22 readies firearm 124, sights, and fires upon the target 322. The process repeats to engage a total of 20 targets, for example, displayed on screen 302.

Scenario 3, Draw, 20-Right: The trainee 22 faces forward, for example, toward screens 304 and 306, a target 322 is displayed on right-hand screen 308, the trainee 22 readies firearm 124, sights, and fires upon the target 322. The process repeats to engage a total of 20 targets, for example, displayed on screen 308.

Scenario 4, Draw, 20-Clap: A target 322 is displayed in a random or preset location on the screens 302-308, the trainee 22 readies firearm 124, for example, drawing it from its holster or otherwise positioning it from a rest to a ready position, sights, fires upon the target 322, returns the firearm 124 to its holster or holster firearm, and claps. This process repeats to engage a total of 20 targets, for example, displayed randomly, for example, on screens 302-308. For example, a predetermined or random but "smooth" distribution pattern that limits the maximum displacement between sequential targets 322 is used.

Scenario 5, Draw, 20-Step: A target 322 is displayed in a random or present location on the screens 302-308, the trainee 22 readies firearm 124, sights, fires upon the target 322, returns the firearm 124 to its rest position, and steps around or over an obstacle 328. This process repeats to engage a total of 20 targets 322 displayed randomly, for example, on screens 302-308.

Scenario 6, 180 Degree Drill: Scenario 6 and the next three scenarios are designed to enhance the trainee's economy of motion, e.g., straight line movement of firearm 124 from one target 322 to the next. A target 322 is displayed on the left screen 302, the trainee fires upon the target 322, and then a subsequent target 322 is displayed about 180 degrees relative to the trainee 22 from the first target 322, for example, on the right screen 308. This process repeats to engage a total of 20 targets, for example with the first of each target set alternating between being displayed on the left screen 302 or the right screen 308.

Scenario 7, 90 Degree Drill: Target 322 are displayed and engaged at about 90 degree increments relative to the trainee 22. For example, a target 322 is displayed on the left screen 302, the trainee fires upon the target 322, a subsequent target 322 is displayed 90 degrees from the first, for example, on the front screens 304-306. After the trainee fires upon the target 322 located on the front screens 304-306, a subsequent target 322 is displayed 90 degrees from that target, for example, on the right screen 308. This process repeats to engage a total of 12 targets, for example, with the first of each target set alternating between being displayed on the left screen 302 or the right screen 308.

Scenario 8, 45 Degree Drill: Targets 322 are displayed and engaged at about 45 degree increments relative to the trainee 22. For example, a target 322 id displayed on the left screen 302, the trainee fires upon the target 322, and a subsequent target 322 is displayed on the front screen 304. After the trainee fires upon the target 322 on screen 304, a subsequent target 322 is displayed on the front screen 306. After the target 322 on screen 306 is engaged, a target 322 is displayed and engaged on screen 308. This process repeats to engage a total of 16 targets, for example, with the first of each target set alternating between being displayed on the left screen 302 or the right screen 308.

Scenario 9, 36 Degree Drill: Targets 322 are displayed and engaged at about 36 degree increments relative to the trainee 22. For example, a target 322 is displayed on the left screen 302, the trainee fires upon the target 322, and a subsequent target 322 is displayed about 36 degrees relative to the trainee 22 and the first target, for example, on the left side of the front screen 304. After the trainee fires upon the target 322 on screen 304, a subsequent target 322 is displayed an addition about 36 degrees, for example, at about the intersection of the front screens 304 and 306. After that target is engaged, a target 322 is displayed at an increment of about another 36 degrees, for example, on the right side of the front screen 306. After that target 322 is engaged, a subsequent target 322 is displayed at an increment of about another 36 degrees, for example, on the right screen 308. This process repeats to engage a total of 15 targets, for example, with the first of each target set alternating between being displayed on the left screen 302 and the right screen 308.

Figure 10:
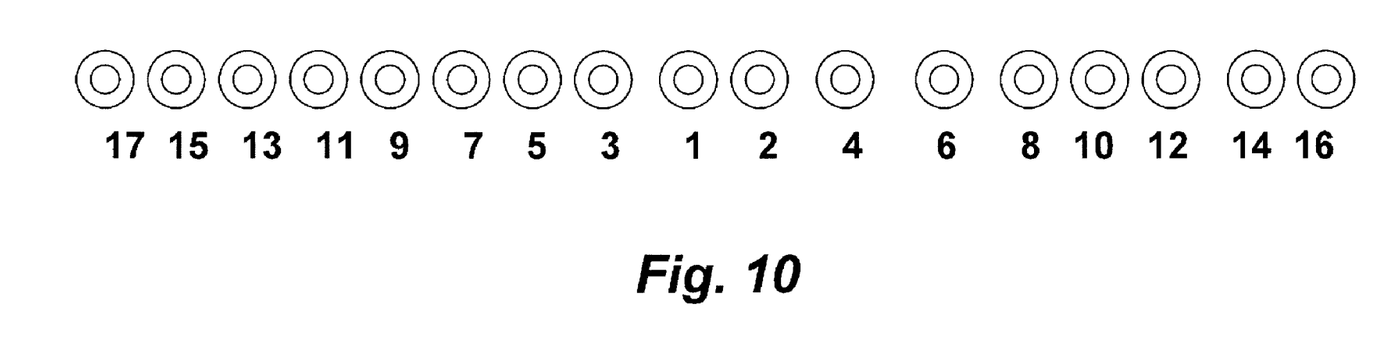
FIG. 10 shows an illustrative target pattern associated with an indexed linear training scenario of the disclosed methods and systems.

Scenario 10, Indexed Linear: The indexed drills condition the trainee 22 to keep the properly indexed in the transition between targets 322, to check the barrel locked in position with the eyes, to use economy of motion, and consistent sight alignment. For example, as shown in FIG. 10, a first target 322 is displayed and engaged at the center of front screens 304 and 306. Each subsequent target 322 is displayed and engaged and incrementally increasing angles left and right of the location of the first target 322 until targets 322 are displayed and engaged both about 90 degrees left and about 90 degrees right of the first target. This process repeats until 57 targets, for example, are displayed and engaged.

Figure 11:
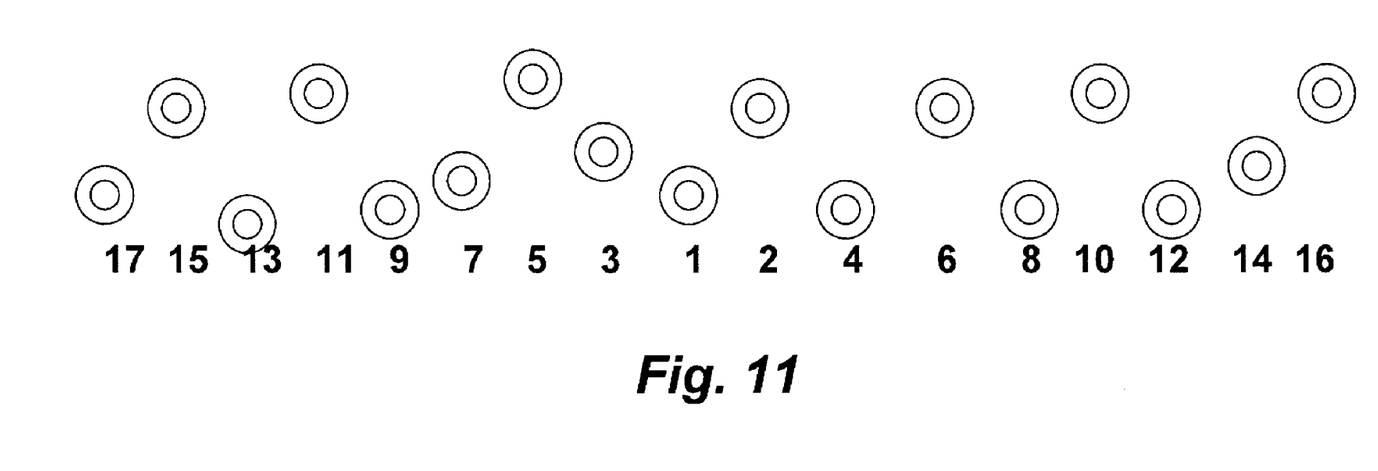
FIG. 11 shows an illustrative target pattern associated with an indexed up and down training scenario of the disclosed methods and systems.

Scenario 11, Indexed Up and Down is another linear target drill for training proper level indexed transition between targets 322. For example, as shown in FIG. 11, a first target 322 is displayed and engaged at the center of front screens 304 and 306. Each subsequent target 322 is displayed and engaged and incrementally increasing angles left and right of the location of the first target 322 and displaced vertically alternatingly up and down until targets 322 are displayed and engaged both about 90 degrees left and about 90 degrees right of the first target. This process repeats until 57 targets, for example, are displayed and engaged.

Figure 12:
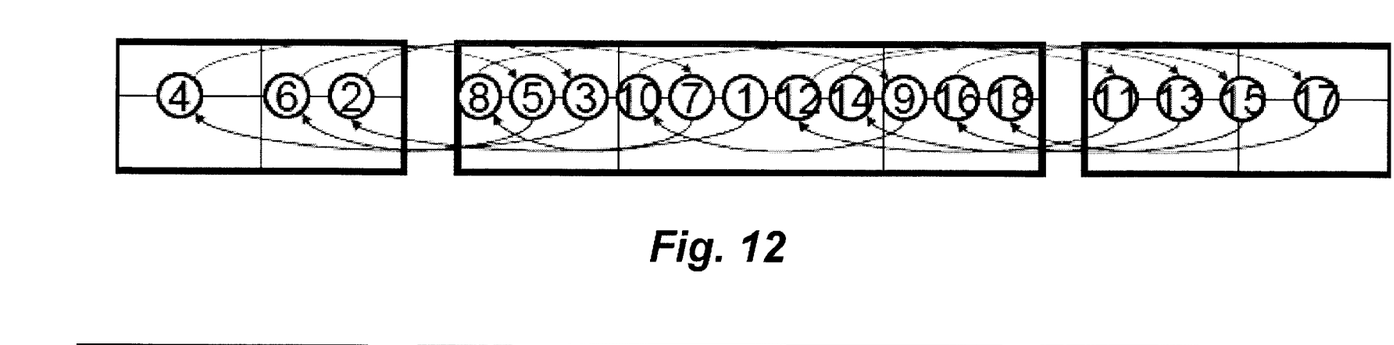
FIG. 12 shows an illustrative target pattern associated with a reverse reflex training scenario of the disclosed methods and systems.

Scenarios 12 and 13, Reverse Reflex Drills: designed to strengthen the backward reflex abilities of the trainee 22. Referring to FIG. 12, trainees engage targets 322 that index a fixed amount, for example 18 feet left (or right), and then the subsequent target 322 is displayed and engaged half that fixed amount in the opposite direction, for example 9 feet right (or left). The scenario strengthens the trainee's ability to react to a threat previously passed by. This process repeats for 37 targets, for example.

Figure 13:
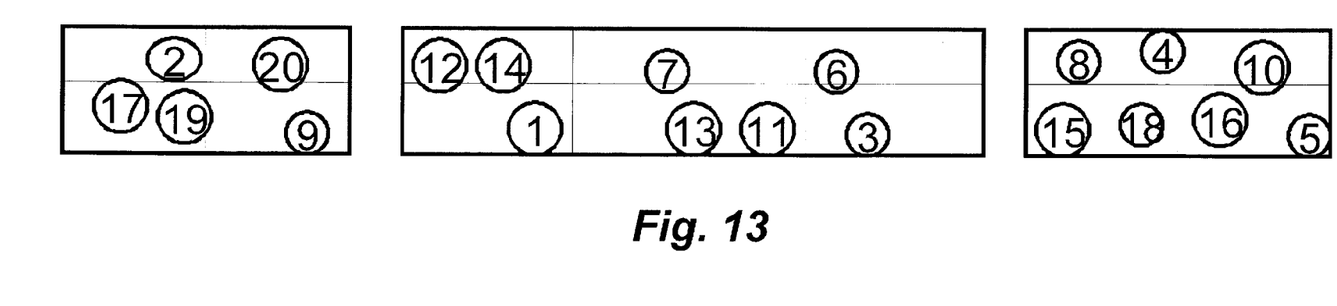
FIG. 13 shows an illustrative target pattern associated with a first random distribution training scenario of the disclosed methods and systems.

Scenario 14, Random 20, Open Mode: Referring to FIG. 13, the trainee 22 engages targets 22 displayed in the open mode, i.e a target 322 remains until successfully engaged, then a subsequent target 322 is displayed. For example, the target pattern shown in FIG. 13 can be used until a total of 20 targets, for example, are engaged.

Figure 14:
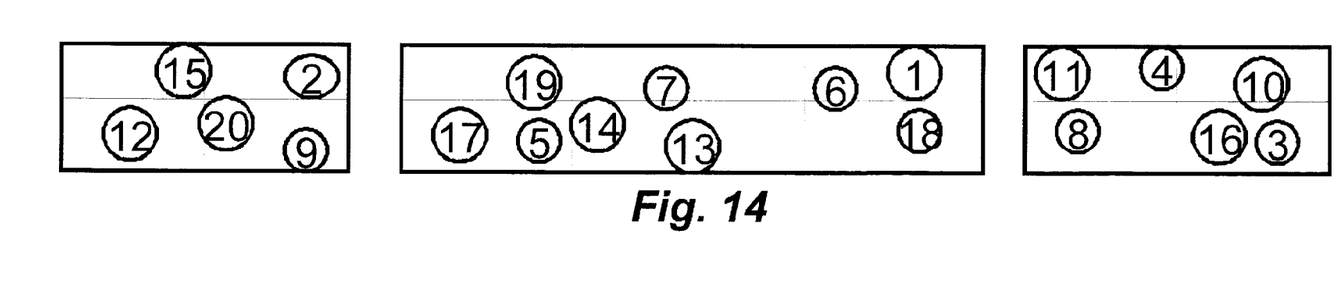
FIG. 14 shows an illustrative target pattern associated with a second random distribution training scenario of the disclosed methods and systems.
Figure 15:
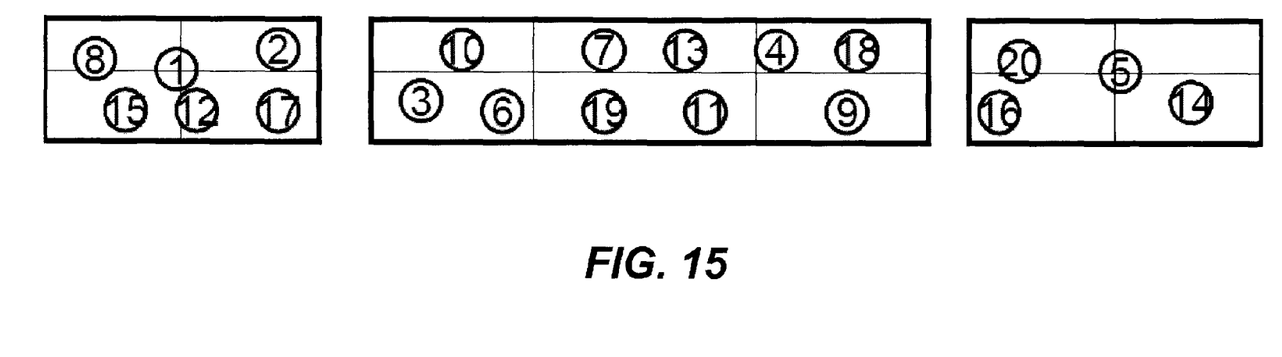
FIG. 15 shows another illustrative target pattern associated with training scenarios of the disclosed methods and systems.

Scenario 15, Random 20, Fixed Mode: Referring to FIG. 14, the trainee 22 engages targets 22 displayed in the fixed mode, i.e. a target 322 remains for a fixed interval, for example about 1.5 seconds, whether successfully engaged or not, then a subsequent target 322 is displayed. For example, the target pattern shown in FIG. 13 can be used until a total of 20 targets, for example, are sequentially displayed Scenario 16, Pattern #1, Fixed Mode at 1.0 second intervals: Twenty targets 322 are sequentially displayed throughout the screens 302-308, for example, using pattern #1 shown in FIG. 15; however, other repeating patterns can be substituted. The targets 322 appear one at a time for the fixed time interval or until successfully engaged. The locations of the targets 322 have been intentionally selected in order to cover the full range of motion up, down, up-left, down-right, straight ahead, and so on. The trainees 22 run through variations of this sequence in the next 10 scenarios. In doing so, the trainee 22 will notice a development of muscle memory and an intuitive ability to turn, sight, and fire. The repetition of this sequence is essential for the trainee 22 developing self confidence and fine tuning target engagement skills.

Scenario 17, Pattern #1, No Shot, Fixed Mode at 0.75 seconds: The trainee 22 only sights and tracks the targets 322, there is no engagement with the firearm 124. The no shot scenarios condition the trainee's ability to quickly sight the targets 322 around the area 326. By eliminating the need to aim and fire the firearm 124, the trainee 22 will gain confidence in his or her ability to track objects at short time intervals, for example 0.50 second.

Scenario 18, Pattern #1, No Shot, Fixed Mode at 0.50 seconds: The trainee 22 only sights and tracks the targets 322, there is no engagement with the firearm 124.

Scenario 19, Pattern #1, No Shot, Fixed Mode at 0.25 seconds: The trainee 22 only sights and tracks the targets 322, there is no engagement with the firearm 124.

Scenario 20, Pattern #1, Fixed Mode, at 1.5 second intervals: Twenty targets 322 are sequentially displayed throughout the screens 302-308. The targets 322 appear one at a time for earlier of the fixed time interval or until successfully engaged. After trying to visually sight and track targets at 0.25 seconds intervals, the trainee 24 should be able to comfortably and successfully engage targets displayed at an interval of 1.5 seconds.

Scenario 21, Pattern #1, Fixed Mode at 1.0 second intervals: Twenty targets 322 are sequentially displayed throughout the screens 302-308. The targets 322 appear one at a time for earlier of the fixed time interval or until successfully engaged.

Scenario 22, Pattern #1, Fixed Mode at 0.75 second intervals: Twenty targets 322 are sequentially displayed throughout the screens 302-308. The targets 322 appear one at a time for earlier of the fixed time interval or until successfully engaged.

Scenario 23, Pattern #1, Fixed Mode at 0.50 second intervals: Twenty targets 322 are sequentially displayed throughout the screens 302-308. The targets 322 appear one at a time for earlier of the fixed time interval or until successfully engaged.

Scenario 24, Pattern #1, Fixed Mode at 1.5 second intervals: Twenty targets 322 are sequentially displayed throughout the screens 302-308. The targets 322 appear one at a time for earlier of the fixed time interval or until successfully engaged.

Scenario 25, 3-5-7 Pattern: Each of multiple sets will sequentially display a target 322 at center, for example on the screens 304 and 306, then to one side, for example on the screen 308. Each target 322 to a side in a set may be progressively further displaced from the target 322 at the center displayed between each shot to the side. The scenario can follow a pattern of how many targets 322 are displayed on each side before progressing to the next set, which for example can be the same number of targets 322 on the opposite side. For example, the pattern, which includes each side target 322 preceded with a target 322 at the center, can be three targets 322 to the right, for example on screen 308, three targets to the left, for example on screen 302, five targets to the right, five targets to the left, seven targets to the right, and seven targets to the left. The targets 322 can be vertically located along the same horizontal line.

Scenario 26, 3-5-7 Pattern Up and Down: can use the same pattern as scenario 25 except that each side and/or center target 322 can vary in its vertical placement in a set or random fashion.

The above listed scenarios are illustrative only and variations or alternative conditioning patterns can be utilized with the systems and methods 20, 100, 200, 300, and 400.

While the invention has been illustrated and described in detail in the foregoing drawings and description, the same is to be considered as illustrative and not restrictive in character, it being understood that only illustrative embodiments thereof have been shown and described and that all changes and modifications that come within the spirit and scope of the invention as defined in the following claims are desired to be protected.

The invention claimed is:

1. A method of conditioning a trainee's firearms skills, comprising the steps of:
   sequentially displaying stimuli of a first plurality of visual stimuli, the first plurality of visual stimuli having an initial stimulus, intervening stimuli, and a final stimulus, each stimulus in the first plurality of visual stimuli having at least one of:
      a speed of movement greater than the speed of movement of an immediately preceding stimulus, and
      a time period of display shorter than the time period of display of an immediately preceding stimulus;
   determining the trainee's success in at least one of sighting, tracking, recognizing, and shooting each of the first plurality of visual stimuli while displayed;
   ceasing display of the first plurality of visual stimuli upon the trainee's success declining below a predetermined threshold, the final stimulus being the last displayed stimulus upon ceasing display;
   sequentially displaying stimuli of a second plurality of visual stimuli, each stimulus of the second plurality of visual stimuli having at least one of:
      a speed of movement exceeding the speed of movement for the final stimulus, and
      a time period of display shorter than the time period of display for the final stimulus;
   sequentially displaying stimuli of a third plurality of visual stimuli, each stimulus of the third plurality of visual stimuli having at least one of:
      a speed of movement less than the speed of movement for the final stimulus and greater than the speed of movement for the initial stimulus, and
      a time period of display longer than the time period of display for the final stimulus and shorter than the time period of display for the initial stimulus; and
   wherein the trainee attempts to at least one of sight, track, recognize, and shoot each stimulus of the first, second, and third plurality of visual stimuli.

2. The method of claim 1, further comprising the steps of:
   determining for the first stimulus at least one of a speed of movement or a time period of display such that the trainee can easily at least one of sight, track, recognize, and shoot the first stimulus; and
   determining for the final stimulus at least one of a speed of movement or a time period of display such that the trainee can not at least one of sight, track, recognize, and shoot the final stimulus.

3. The method of claim 2, wherein the determining steps are based at least in part on the particular trainee's firearms skills.

4. The method of claim 2, further comprising the step of determining for the third plurality of stimuli at least one of a speed of movement or a time period of display such that the trainee can at least one of sight, track, recognize, and shoot the stimulus of the third plurality of stimuli.

5. The method of claim 4, wherein the step of determining for the third plurality of stimuli is based at least in part on the particular trainee's firearms performance in at least one of sighting, tracking, recognizing, and shooting the stimuli of the first plurality of stimuli.

6. The method of claim 1, wherein the time period of display for the initial stimuli is about 1.5 seconds or longer.

7. The method of claim 1, wherein the time period of display for the final stimuli is about 0.25 seconds or shorter.

8. The method of claim 1, wherein the speed of movement relative to the trainee of the initial stimulus is about 10 degrees/second or slower.

9. The method of claim 1, wherein the speed of movement relative to the trainee of the final stimulus is about 100 degrees/second or faster.

10. The method of claim 1, further comprising the step of determining the trainee's performance in sighting and tracking stimuli at least in part by comparing data from an ocular tracking device directed at a trainee's eye with the location of the stimuli relative to the trainee's eye.

11. The method of claim 1, wherein the trainee's attempts to shoot each stimulus of the first, second, and third plurality of visual stimuli includes the trainee using a laser equipped firearm to shoot at the stimuli; and further comprising the step of determining the trainee's performance in shooting stimuli at least in part by comparing the timing and location of a laser spot fired by the trainee with the timing and location of the stimuli.

12. A method of conditioning a trainee's firearms skills, comprising the steps of:
   sequentially presenting a first plurality of target scenarios, each target scenario have a plurality of targets;
   for each target scenario presented in the first plurality of target scenarios, displaying sequentially each target for a period of time, the period of time associated with each subsequent target scenario shorter than the period of time associated with an immediately preceding target scenario;
   determining the trainee's success in shooting each target while displayed;
   ceasing display of the first plurality of target scenarios upon the trainee's success in shooting targets declining below a predetermined threshold;
   sequentially presenting a second plurality of target scenarios, the second plurality of target scenarios having at least a plateau target scenario and a final target scenario, each of the plateau and final target scenarios have a plurality of targets;
   sequentially displaying each target of the plateau target scenario, the targets of the plateau target scenario displayed for a period of time shorter than the shortest period of time used for the first plurality of target scenarios;
   selecting a final period of time that is greater than the period of time associated with the targets of the plateau target scenario and less than the period of time of a first target scenario of the first plurality of target scenarios; and sequentially displaying each target of the final target scenario for the final period of time.

13. The method of claim 12, wherein the time period of time associated with the plateau target scenario is about 0.25 seconds or shorter.

14. The method of claim 12, wherein a target location pattern is associated with each target scenario, the target location patterns such that each target is displayed in a location different from an immediately preceding target.

15. The method of claim 1, wherein a display location pattern is associated with each stimuli of the third plurality of visual stimuli, the display location pattern of each stimuli of the third plurality of visual stimuli is different from the display location pattern of an immediately preceding stimuli of the third plurality of visual stimuli.

16. A method of conditioning a trainee's firearms skills, comprising the steps of:
   sequentially presenting a first plurality of target scenarios, each target scenario have a plurality of targets;
   for each target scenario presented in the first plurality of target scenarios, displaying sequentially each target, a speed of movement associated with each subsequent target scenario faster than the speed of movement associated with an immediately preceding target scenario;
   determining the trainee's success in shooting each target while displayed;
   ceasing display of the first plurality of target scenarios upon the trainee's success in shooting targets declining below a predetermined threshold;
   sequentially presenting a second plurality of target scenarios, the second plurality of target scenarios having at least a plateau target scenario and a final target scenario, each of the plateau and final target scenarios have a plurality of targets;
   sequentially displaying each target of the plateau target scenario, the targets of the plateau target scenario having a speed of movement faster than the fastest speed of movement used for the first plurality of target scenarios;
   selecting a final speed of movement that is slower than the speed of movement associated with the targets of the plateau target scenario and faster than the speed of movement of a first target scenario of the first plurality of target scenarios; and
   sequentially displaying each target of the final target scenario using the final speed of movement.

17. The method of claim 16, wherein the speed of movement associated with the plateau target scenario is about 100 degrees/second or faster.

18. The method of claim 16, wherein a target location pattern is associated with each target scenario, the target location patterns such that each target is displayed in a location different from an immediately preceding target.

* * * * *